United States Patent [19]

O'Keefe, III

[11] Patent Number: 4,602,905
[45] Date of Patent: Jul. 29, 1986

[54] DENTAL IMPRESSION REGISTRATION DEVICE

[76] Inventor: John T. O'Keefe, III, 7514 Second Ave. NE., Seattle, Wash. 98115

[21] Appl. No.: 716,335

[22] Filed: Mar. 26, 1985

[51] Int. Cl.$^4$ .............................................. A61C 9/00
[52] U.S. Cl. ........................................ 433/41; 433/214
[58] Field of Search ......................... 433/41, 214, 42

[56] References Cited

U.S. PATENT DOCUMENTS

| | | | |
|---|---|---|---|
| Re. 28,667 | 12/1975 | Gores | 128/136 |
| 968,055 | 8/1910 | Howard | 433/42 |
| 2,001,963 | 5/1935 | Keller | 433/42 |
| 2,696,668 | 12/1954 | Fox | 433/42 |
| 2,895,219 | 7/1959 | Jones | 433/38 |
| 3,026,614 | 3/1962 | Squillace et al. | 433/71 |
| 3,064,354 | 11/1962 | Pos | 433/71 |
| 3,085,337 | 4/1963 | Shulman | 433/38 |
| 3,131,475 | 5/1964 | Craigo et al. | 433/71 |
| 3,161,956 | 12/1964 | Van Court et al. | 433/71 |
| 3,200,497 | 8/1965 | Goodfriend | 433/44 |
| 3,228,107 | 1/1966 | Zandberg | 433/71 |
| 3,468,029 | 9/1969 | Moore | 433/38 |
| 3,501,837 | 3/1970 | Clark | 227/94 |
| 3,541,690 | 11/1970 | Cerveris | 433/42 |
| 3,574,259 | 4/1971 | Jones | 433/38 |
| 3,736,663 | 6/1973 | White | 433/38 |
| 3,822,473 | 7/1974 | Jones | 433/38 |
| 3,903,602 | 9/1975 | Jones | |
| 4,003,132 | 1/1977 | Beck | 433/42 |
| 4,016,650 | 4/1977 | Leusner et al. | 433/42 |
| 4,161,067 | 7/1979 | Bekey et al. | 433/42 |
| 4,204,323 | 5/1980 | Neubert | 433/38 |
| 4,376,628 | 3/1983 | Aardse | 433/80 |
| 4,432,728 | 2/1984 | Skarky | 32/17 |
| 4,445,854 | 5/1984 | Bekey | 433/37 |
| 4,449,927 | 5/1984 | Taylor et al. | 433/38 |
| 4,472,140 | 9/1984 | Lustig | 433/38 |

Primary Examiner—Robert Peshock
Attorney, Agent, or Firm—Christensen, O'Connor, Johnson & Kindness

[57] ABSTRACT

A device for producing precisely registered upper and lower dental impressions includes an impression tray having upper and lower impression cavities for receiving impression material. A slidably movable registration tab is located within the lower cavity to provide a guide for repositioning the lower jaw to a desired position. A simultaneous facebow transfer is an integral part of the device permitting an accurate relationship of upper and lower dental arches to the paired temporomandibular joints.

9 Claims, 5 Drawing Figures

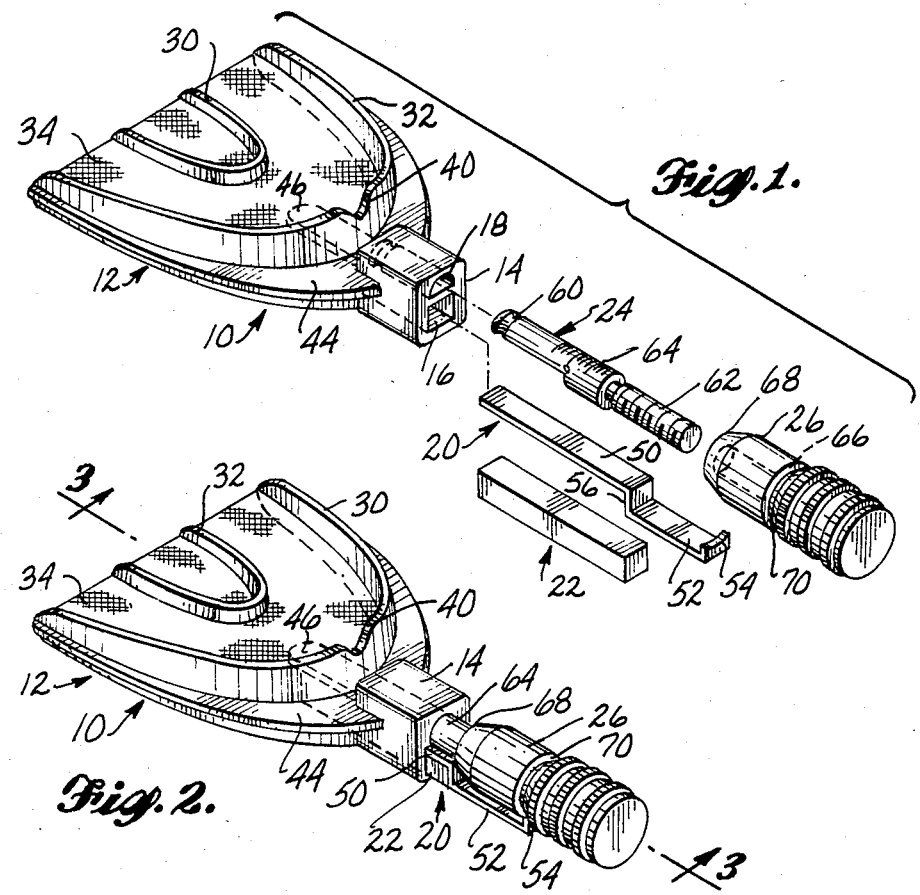
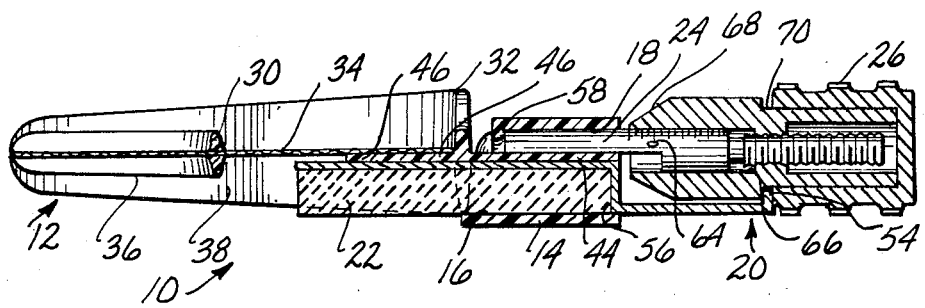

DENTAL IMPRESSION REGISTRATION DEVICE

FIELD OF THE INVENTION

The present invention relates generally to methods and apparatus for producing dental impressions and, more particularly, to a device for taking impressions of the upper and lower dental arches which incorporates a sliding index for registering a precise relationship of the lower jaw to the upper and of the upper jaw to the axis-orbital plane of the head.

BACKGROUND OF THE INVENTION

The temporomandibular joint articulates the mandible (the lower jawbone) to the temporal bone of the skull. If the female and male portions of the temporomandibular joint of an individual are misaligned or if the joint or the interposed disc is damaged or destroyed, pain and altered function may result. One technique used to relieve joint pressure and reposition the members of the joint involves the construction of a splint or a removable intraoral appliance into which the upper and lower teeth fit in such a manner as to realign and reposition the members of the temporomandibular joint in an attempt to relieve joint pressure, provide relaxation of the jaw muscles and allow healing of the joint.

A splint is typically molded from a thermoplastic or thermosetting polymer and contains on its upper and lower surfaces a reverse image or impression of the upper teeth and the lower teeth. Stone models or casts are made from these impressions of the upper and lower teeth. These casts must then be positioned or registered relative to each other so as to achieve a desired relationship in the temporomandibular joint. Traditionally, splints have been made by first taking separate impressions of the upper and lower teeth utilizing conventional techniques. An intraocclusal bite record is then usually made by placing a relatively thin sheet of wax or other bite registration material between the patient's teeth and having the patient bite in the desired jaw relationship. This procedure involves a separate step utilizing the registration material which is subsequently interposed between the dental casts or models of the teeth to align the models in the desired relationship. This conventional step of relating dental casts with a separate interposed bite registration material for the purpose of producing splints, or for other occlusal therapy, introduces inaccuracies because inherent distortion of the wax or other bite registration material, especially from temperature changes, may result in an inaccurate mounting or relationship of the patient'dental casts. The multiple steps involved in handling the separate bite registration material also lead to additional distortion of the relationship between the mounted casts.

Mounting the lower dental cast to the upper cast requires a separate step which is a facebow transfer. A facebow is positioned on the patient's head relative to the axis-orbital plane which relates the location of the upper dental arch to the temporomandibular joint. The facebow is then transferred to an articulator, a machine used to simulate jaw function. The model made from the impression of the upper teeth can then be positioned on the articulator utilizing the facebow. This separate step also introduces the possibility of distortion of the mounting. Thereafter, the model made from the impression of the lower teeth is positioned against the upper model using the intraocclusal bite record. Completion of these separate steps and mounting of the dental casts on the articulator yields a rigid mechanical analog of an individual's jaw movements and relationships.

If, for example, it is desired to make a splint in which the patient's lower jaw is moved two millimeters forward of its normally closed position to relieve pressure on the temporomandibular joint, the model of the lower teeth is moved forward relative to the model of the upper teeth and affixed at the new position. A splint is then produced from the repositioned location of the models of the upper and lower teeth. As one might surmise, this repositioning can introduce several inaccuracies into the splint. As a result, when a splint is fitted to a patient's teeth, a significant amount of time and effort may be required in order to obtain a final accurate relationship of the paired temporomandibular joints and the upper and lower teeth relative to the splint. This same registration technique described herein is applicable to recording jaw positions and relationships for fabrication of removable orthodontic appliances, for relating complete dentures, for mounting dental casts for diagnostic purposes including bite adjustments and for fabrication of single or multiple units of fixed or removable prosthetics.

SUMMARY OF THE INVENTION

The present invention provides a device for quickly and accurately producing impressions of the upper and lower teeth that are precisely registered in a desired position relative to each other. This result is accomplished by incorporating the previously separate steps of obtaining a bit registration, a facebow transfer and impressions into one accurate step. Use of the device significantly increases the accuracy of the procedure and reduces the time normally required by a dentist in fitting the splint, orthodontic appliance or dental prosthesis.

The apparatus for registration of upper and lower dental impressions broadly comprises a tray having means defining upper and lower impression cavities divided by a septum. An adjustable bite registration tab is mounted for posterior/anterior movement, preferably in the lower cavity. In one embodiment, the tray includes in its anterior portion a channel that extends from an anterior opening in a posterior direction onto the inferior aspect of the septum. The registration tab is mounted in the channel. A means can also be provided for selectively and slidably moving the tab in the channel. In this embodiment, a separate channel on the superior aspect of the anterior portion of the handle receives the facebow transfer device such that all necessary measurements, bite registrations and tooth impressions are incorporated into a single accurate unit.

In a preferred embodiment, a deformable registration medium, for example, deformable dental wax or other bite registration material is mounted on and affixed to the registration tab. Dental impression material is then placed in the upper cavity and the device is then properly positioned in the patient's mouth to take an impression of the upper teeth. After the upper impression is taken, the registration tab located in the lower cavity is moved to a preselected position in either a posterior or anterior direction and the bite registration obtained. In the preferred embodiment, the registration tab is positioned on the lower side of the septum. The lower impression may then be obtained in the precise jaw position determined by the registration tab into which the patient has previously created an indentation in the registration material with their lower incisors. Prior to taking the lower impression, the indentation can be selectively moved forward or backward in the channel so that the location of the indentation corresponds to the desired relocation of the patient's lower jaw. This method permits nearly full closure of the jaw when desired, or, when indicated for therapeutic purposes, the bite registration can be registered at an increased opening without creating a distortion in the three-dimensional relationship of the mounted dental casts. Once the lower impression material has achieved dimensional stability, a facebow transfer is performed utilizing a connector rod between the impression device and the facebow. The present invention encompassing accurate impressions, jaw relationships and orientation to the jaw joints is removed as a single unit, thus greatly minimizing the potential inaccuracies common with the traditional procedure, which utilizes multiple physically separate procedures which must then be subsequently related to each other.

BRIEF DESCRIPTION OF THE DRAWINGS

FIG. 1 is an exploded isometric view of the impression registration device of the present invention;

FIG. 2 is an isometric view of an assembled registration device constructed in accordance with the present invention;

FIG. 3 is a longitudinal section along a vertical plane through the registration device depicted in FIG. 2; and, FIGS. 4 and 5 are longitudinal sectional views showing the use of the impression device in producing precisely registered impressions of the upper and lower teeth.

DESCRIPTION OF THE INVENTION

Figure 4:
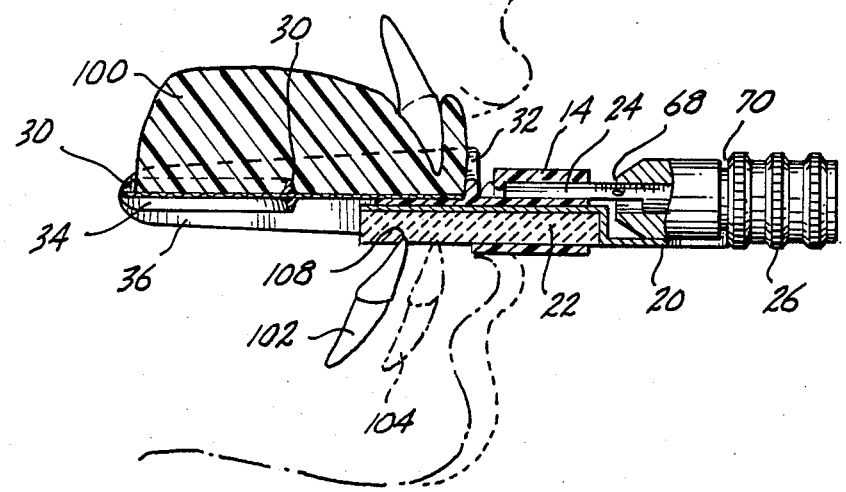
Figure 5:
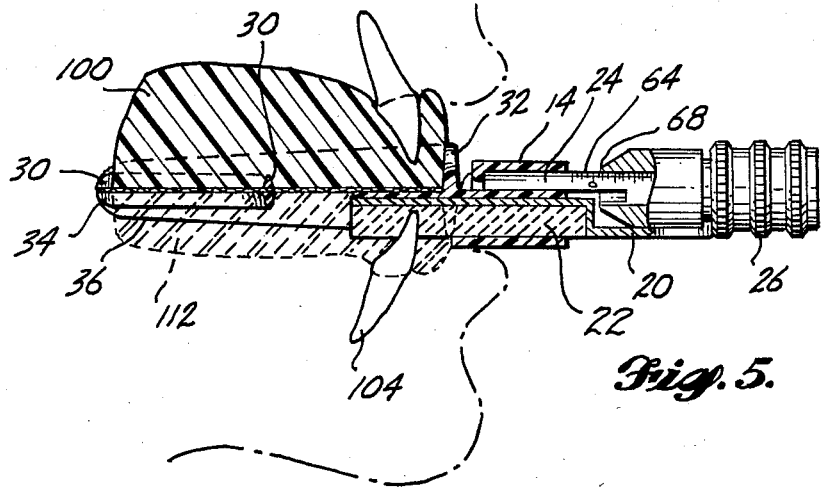

Referring first to FIG. 1, the impression device generally designated 10 includes a double-sided impression tray 12 having an anterior reinforcing enlargement 14 through which first and second channels 16 and 18 extend in an anterior/posterior direction. The first channel 16 is shaped to receive a flat registration tab 20 onto which can be positioned a deformable registration material 22, such as ordinary dental wax. The registration tab preferably has a width slightly less than the lateral extent of the lower incisors. The upper channel 18 removably receives a reciprocator rod 24. A reciprocator knob 26 threadably engages the reciprocator rod. The registration tab 20 and the reciprocator knob coact so that selective rotation of the knob will selectively reciprocate the registration tab in the registration channel 16.

Referring now collectively to FIGS. 1, 2 and 3, the impression tray 12 is generally symmetrical about a posterior or anterior axis and has two U-shaped ridges 30 and 32 on the upper side of a septum 34 and mirror image ridges 36 and 38 extending downwardly from the lower side of the septum. The sides of the ridges extend in a posterior direction and terminate adjacent the posterior edge of the septum 34. The first set of ridges 30 and 32 are spaced substantially equidistantly from each other and with the septum 34 define an upper impression cavity. Similarly, the lower ridges 36 and 38 in conjunction with the septum 34 form a lower impression cavity. The shape and spacing of the upper and lower ridges can be varied to provide cavities of different sizes as desired. A notch 40 that extends downwardly from the upper ridge of the anterior ridge 32 is positioned at the anterior central end of the ridge 32. A reinforcing flange 44 extends forwardly from the anterior ridges 32 and 38 substantially adjacent the plane of the septum 34. A tabular reinforcing flange 46 also extends rearwardly from the anterior ridges 32 and 38, and in the preferred embodiment, lies beneath the septum 34. The tabular flange 46 preferably has a width that is substantially equal to the width of the registration tab 20.

A reinforcing enlargement 14 is integrally constructed with the forwardly extending reinforcing flange 44. The enlargement 14 extends upwardly and downwardly from the reinforcing flange 44 and has a width approximately twice that of the reinforcing flange 46. The reinforcing enlargement 14 extends forwardly from the anterior edge of the reinforcing flange 44. The reinforcing enlargement carries the upper and lower channels 16 and 18. The lower channel 16 has an upper surface that is coplanar with the bottom surface of the tabular flange 46 that extends into the lower impression cavity. The lower channel 16 extends from an anterior opening on the anterior face of the reinforcing enlargement 14 rearwardly through the lower anterior flange 38 and opens into the lower impression cavity adjacent the lower surface of the tabular flange 46. In the preferred embodiment, the registration channel 16 has a rectangular cross section for receiving registration tab 20 and the deformable registration material 22.

In the preferred embodiment, the registration tab comprises a rectangular tab that slidably engages the upper surface of the registration channel 16 and the coplanar lower surface of the reinforcement flange 46. The rectangular tab 50 has an anterior extension 52 that extends first downwardly from the anterior edge of the tab 50, then extends forwardly and terminates in an upwardly oriented flange 54, the purpose of which will be described in more detail below. The posterior surface of the extension 52 provides an abutment shoulder 56 for the anterior surface of the deformable registration material 22. The registration material preferably is in the form of a right rectangular polyhidron and is adhered to the lower surface of the tab 50 by its natural adhesive characteristics. Alternatively, a conventional adhesive can be employed to secure the registration material to the lower surface of the tab 50. Thus the tab 20 and registration material 22 slidably and reciprocably engage the registration channel 16 as a unit.

The second channel 18 is positioned above the lower channel 16 and has in the preferred embodiment a semicircular cross section. The posterior portion of the channel 18 carries a downwardly extending nib 58 which in conjunction with an annular channel 60 in the rod 24 secures the rod 24 in the channel 18 in a predetermined position. The posterior end of the rod 24 has a semicircular cross section that fits snugly into the channel 18. The anterior end of the rod carries a cylindrically shaped threaded portion 62. Between the threaded portion 62 and the posterior end of the rod are located a plurality of axially spaced indicia running in a circumferential direction relative to the rod. The indicia are preferably positioned at axial spacings of one millimeter or predetermined fractions thereof. The reciprocator knob 26 has an internal bore 66 that is threaded to receive and engage the threaded portion 62 of the rod 24. Posterior end 68 of the knob 26 terminates adjacent the indicia 64 on the rod 24. As the rod is rotated, the posterior end 68 reciprocates relative to the rod 24, the indicia provide a relative location of the knob to the rod. At its midpoint, the knob 26 also carries an exterior annular channel 70. The flange 54, forming part of the registration tab 20, is constructed so as to slidably engage the channel 70. Thus, as the knob 26 is rotated and reciprocates on the rod 24, the registration tab 20 is also moved or reciprocated within the channel 16.

Preferably, the indicia on the rod 24 are arranged so as to include a "zero" position identified by the numeral "0" on the rod. Before using the registration device, the posterior end 68 of the knob 26 is positioned so that it is located adjacent the zero position. In this manner, relative movement of the deformable material 22 relative to the upper mold cavity can be precisely measured during the process of producing registered impressions of the upper and lower teeth. For example, the threads on the rod 24 can be constructed and arranged so that one rotation of the knob 26 will axially move the knob one millimeter, resulting in a one millimeter movement of the registration tab.

Referring now to FIG. 4, use of the registration device to produce precisely registered upper and lower teeth impressions will be described. First, the knob 26 is set at its zero position relative to the indicia on the rod 24. This knob setting locates the deformable registration material 22 at a predetermined location relative to the upper cavity. Thereafter, settable impression material 100 is distributed in the upper impression cavity of the tray 12. The tray is then inserted in the patient's mouth so as to take an impression of the upper teeth utilizing what are otherwise conventional techniques. Once the mold material 100 is set, the patient is caused to bite with his or her lower incisors partway through the deformable registration material 22 with his or her jaw in its normal position, i.e., without causing the patient to move his or her jaw forwardly or rearwardly from its natural position. The natural position is indicated in FIG. 4 by the location of lower incisor 102. Thereafter, the patient is caused to move his or her jaw forwardly or rearwardly so as to position the lower jaw at a desired position to relieve pressure on and/or reposition the members of the temporomandibular joint, or for achieving mounted dental casts for construction of removable orthodontic appliances, fixed and removable prosthetics, dentures, or diagnostic analysis of dental occlusion. This desired position is indicated by the dotted outline of the incisor 104, which is, for example, located forwardly of the natural position of the incisor 102. Once the desired position of the incisor 104 is located, the reciprocator knob 26 is turned until the notch 108 formed in the deformable material 22 is located adjacent the desired location of the incisor 104. As the notch 108 is moved forwardly, the posterior end 68 of the knob also moves relative to the indicia on the rod 24 providing a measurement of the desired forward movement of the lower jaw.

Thereafter, the registration device is removed from the patient's mouth and settable impression material 112 is applied to the lower impression cavity. The device 10 is then reinserted in the patient's mouth so that the upper impression material reengages the upper teeth. The patient is thereafter asked to locate the notch 108 in the deformable material 22 by moving his jaw forwardly from its natural position to the desired position. Thereafter the patient is caused to bite fully into the deformable material 22 without moving his or her jaw forwardly or rearwardly. Thereafter the settable material 112 is allowed to set.

The registration device constructed in accordance with the preferred embodiment can also be utilized for obtaining a facebow transfer to determine the location of the temporomandibular joint relative to the upper teeth. This is accomplished by removing the reciprocator rod 24 from the upper channel 18. A substitute connector rod having a posterior end similar to that of rod 24 but having an anterior end designed to fit into a conventional facebow can then be inserted in the channel 18. Once the facebow transfer is taken, the impression material in the lower impression cavity is set and the entire device can be removed from the patient's mouth.

The impressions of the upper and lower teeth thus produced are in precise registration with each other and provide a mold from which a splint, orthodontic appliance, denture, or prosthetic unit can be made without proceeding through the plurality of steps required to produce a related set of dental casts in accordance with the prior art. Moreover, the molds thus produced are precisely registered so that the inaccuracies and imprecisions of prior techniques are avoided.

In addition, the registration device can be employed to provide registration not only along anterior/posterior and vertical planes but in the transverse plane as well. If desired, the patient's jaw can be moved laterally prior to making the preliminary notch 108 in the deformable bit registration tab. The indentations made by the lower incisors and their embrasures are then used as a guide to laterally reposition the patient's jaw when making the lower impression.

The present invention has been described in accordance with a preferred embodiment and variations thereof. One of ordinary skill will be able to effect changes to the disclosed embodiments, various substitutions of equivalents, and other alterations without departing from the broad concepts disclosed. It is therefore intended that the projection afforded by Letters Patent hereon be limited only by the definition contained in the appended claims and equivalents thereof.

The embodiments of the invention in which an exclusive property or privilege is claimed are defined as follows:

1. An apparatus for registration of upper and lower dental impressions comprising:
 a tray having upper and lower surfaces including upper means defining an upper impression cavity and lower means defining a lower impression cavity positioned below and adjacent said upper impression cavity, said impression cavities being separated by a septum and being relatively immovable;
 a registration tab for relatively locating the upper and lower impressions in a corrected position and means mounting said registration tab for movement relative to said tray in a posterior and anterior direction, said tab being positioned adjacent said septum, said tab including means for receiving a deformable impression registration medium; and
 means for selectively slidably moving said tab in said channel.

2. The apparatus of claim 1, wherein said means mounting said registration tab comprises means defining a channel located on the anterior portion of said tray and lying adjacent the interior aspect of said septum having an anterior opening and extending from said opening in a posterior direction adjacent said septum.

3. The apparatus of claim 2, wherein said registration tab comprises a relatively flat bar mounted for reciprocation in said channel adjacent said septum, said apparatus further comprising a deformable impression material affixed to the exposed surface of said bar for reciprocation with said bar, said material being disposed so that the front teeth of a patient can deform said material when the patient moves his jaws together.

4. The apparatus of claim 3, wherein said means for moving said tab comprises a rotatable member affixed to the anterior portion of said tray, said rotatable member being operably associated with said tab so that upon rotation thereof, said tab is moved in said channel.

5. The apparatus of claim 4, wherein said rotatable member includes a rod removably affixed to the anterior portion of said tray, the rotatable member being threadably engaging said rod so that said rotatable member reciprocates relative to said rod as said threadable member is rotated in first and second directions, said tab being operatively coupled to said rotatable member so that said tab reciprocates with said rotatable member.

6. The apparatus of claim 5, wherein said rod carries a plurality of indicia spaced axially along said rod to indicate linear movement of said rotatable member on said rod and thus linear movement of said tab relative to said tray.

7. The apparatus of claim 1, further comprising means for receiving a facebow connector.

8. An apparatus for registration of upper and lower dental impressions comprising:

a tray having upper and lower surfaces including upper means defining an upper impression cavity and lower means defining a lower impression cavity positioned below and adjacent said upper impression cavity, said impression cavities being separated by a septum and being relatively immovable;

a registration tab and means mounting said registration tab for movement relative to said tray in a posterior and anterior direction, said tab being positioned adjacent said septum, said tab including means for locating the incisors of one jaw in a corrected position relative to the other jaw; and means for selectively slidably moving said tab in said channel.

9. A method for registering upper and lower dental impressions comprising the steps of:

making a first impression of either of the upper or lower sets of teeth;

relocating the other of the upper and lower sets of teeth in a predetermined position relative to the first impression while said first impression is in the patient's mouth; and while said first impression is in the patient's mouth, making an impression of the other of the upper and lower sets of teeth that is immovably affixed to the first impression.

* * * * *